(12) United States Patent
Hete et al.

(10) Patent No.: US 8,359,079 B2
(45) Date of Patent: Jan. 22, 2013

(54) PULSE OXIMETRY SYSTEM AND TECHNIQUES FOR DERIVING CARDIAC AND BREATHING PARAMETERS FROM EXTRA-THORACIC BLOOD FLOW MEASUREMENTS

(75) Inventors: Bernard F. Hete, Kittanning, PA (US); Eric W Starr, Allison Park, PA (US); Eric J Ayers, Alliquippa, PA (US)

(73) Assignee: Starr Life Sciences Corporation, Oakmont, PA (US)

( * ) Notice: Subject to any disclaimer, the term of this patent is extended or adjusted under 35 U.S.C. 154(b) by 1493 days.

(21) Appl. No.: 11/858,879

(22) Filed: Sep. 20, 2007

(65) Prior Publication Data

US 2008/0076992 A1 Mar. 27, 2008

Related U.S. Application Data

(60) Provisional application No. 60/826,530, filed on Sep. 21, 2006.

(51) Int. Cl.
*A61B 5/1455* (2006.01)

(52) U.S. Cl. .................................. 600/324; 600/310

(58) Field of Classification Search ........... 600/309–344
See application file for complete search history.

(56) References Cited

U.S. PATENT DOCUMENTS

| | | | |
|---|---|---|---|
| 4,016,557 A | 4/1977 | Zitelli et al. | |
| 4,032,784 A | 6/1977 | Rich | |
| 4,621,643 A | 11/1986 | New, Jr. et al. | |
| 4,700,708 A | 10/1987 | New, Jr. et al. | |
| 4,830,014 A | 5/1989 | Goodman et al. | |
| 4,958,139 A | 9/1990 | Hyatt | |
| 5,005,142 A | 4/1991 | Lipchak et al. | |
| 5,157,348 A | 10/1992 | Deveau | |
| 5,273,036 A * | 12/1993 | Kronberg et al. | 600/310 |
| 5,692,497 A | 12/1997 | Schnitzer et al. | |
| 5,766,127 A * | 6/1998 | Pologe et al. | 600/310 |
| 5,844,430 A | 12/1998 | Thurnau et al. | |
| 5,860,918 A * | 1/1999 | Schradi et al. | 600/300 |
| 6,032,109 A | 2/2000 | Ritmiller, III | |
| 6,064,898 A | 5/2000 | Aldrich | |
| 6,067,467 A | 5/2000 | John | |
| 6,123,072 A | 9/2000 | Downs | |
| 6,159,147 A | 12/2000 | Lichter et al. | |
| 6,429,718 B1 | 8/2002 | Lauter et al. | |
| 6,448,914 B1 | 9/2002 | Younis et al. | |
| 6,473,008 B2 | 10/2002 | Kelly et al. | |
| 6,536,430 B1 | 3/2003 | Smith | |
| 6,560,976 B2 | 5/2003 | Jayanth | |
| 6,637,434 B2 | 10/2003 | Noble | |
| 6,702,752 B2 | 3/2004 | Dekker | |
| 6,709,402 B2 | 3/2004 | Dekker | |
| 6,805,673 B2 | 10/2004 | Dekker | |
| 6,896,661 B2 | 5/2005 | Dekker | |
| 7,740,591 B1 * | 6/2010 | Starr et al. | 600/534 |
| 2003/0145854 A1 | 8/2003 | Hickle | |
| 2004/0260186 A1 | 12/2004 | Dekker | |
| 2005/0049470 A1 | 3/2005 | Terry | |

* cited by examiner

*Primary Examiner* — Eric Winakur
*Assistant Examiner* — Marjan Fardanesh
(74) *Attorney, Agent, or Firm* — Blynn L. Shideler; Krisanne Shideler; BLK Law Group

(57) ABSTRACT

Medical devices and techniques derive breath rate, breath distention, and pulse distention measurements of a subject from a pulse oximeter system coupled to a subject. These parameters, together with the conventional physiologic parameters obtained from a pulse oximeter system, can be used to assist in controlling the ventilation levels and the anesthesia levels of the subject. The development has human applications and particular applications for animal research.

16 Claims, 7 Drawing Sheets

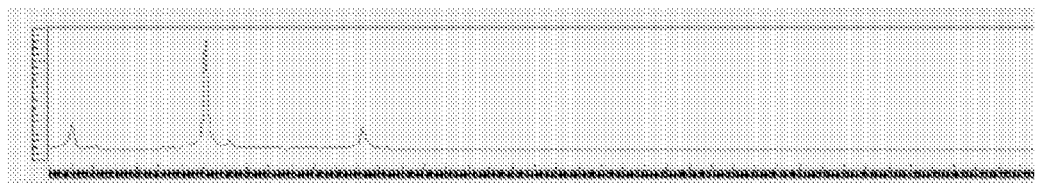
FIG. 5  RAW TIME-DOMAIN INFRARED SIGNAL
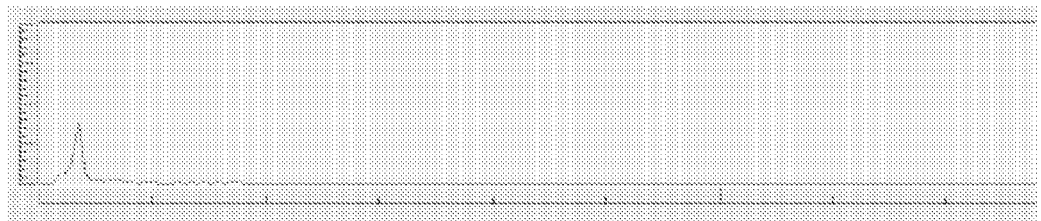
FIG. 6  FFT OF RAW INFRARED SIGNAL
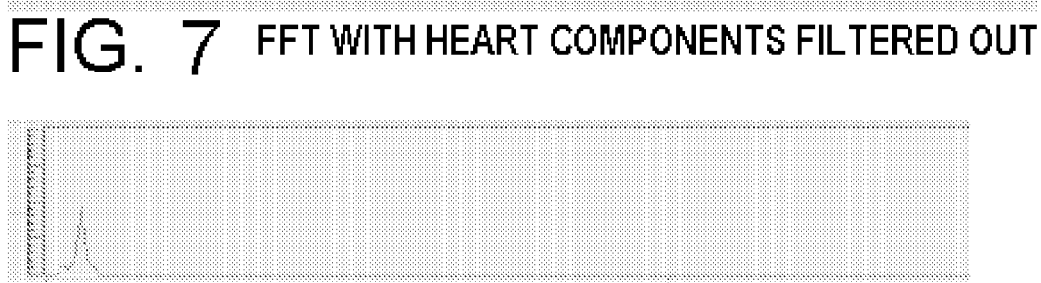
FIG. 7  FFT WITH HEART COMPONENTS FILTERED OUT
FIG. 8  WITH BREATH COMPONENT FILTER APPLIED
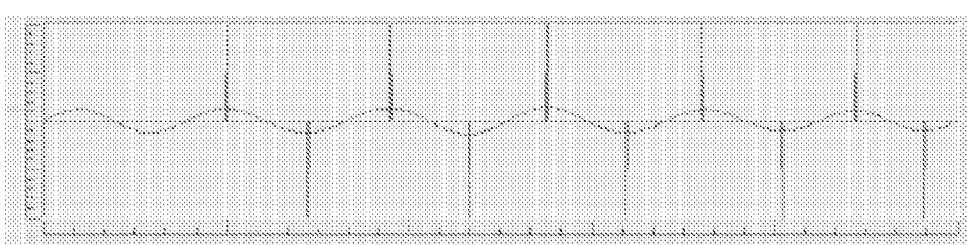
FIG. 9  RECONSTRUCTED BREATH SIGNAL USED TO CALCULATE BREATH RATE

BREATH SIGNAL AND COMBINED
HEART SIGNAL DISPLAY

PULSE AND BREATH DISTENSION
MEASUREMENT DISPLAY

PULSE OXIMETRY SYSTEM AND TECHNIQUES FOR DERIVING CARDIAC AND BREATHING PARAMETERS FROM EXTRA-THORACIC BLOOD FLOW MEASUREMENTS

RELATED APPLICATIONS

The present application claims the benefit of provisional patent application Ser. No. 60/826,530 entitled "Medical Devices and Techniques for Deriving Cardiac and Breathing Parameters from Extra-thoracic Blood Flow Measurements and for Controlling Anesthesia Levels and Ventilation Levels in Subjects" filed Sep. 21, 2006.

BACKGROUND OF THE INVENTION

1. Field of the Invention

The present invention relates to pulse oximeter techniques for deriving cardiac and breathing parameters of a subject from extra-thoracic blood flow measurements, in particular the invention relates to medical devices and techniques for deriving breath rate, breath distention, and pulse distention measurements of a subject from a pulse oximeter system coupled to the subject.

2. Background Information

As background, one type of non-invasive physiologic sensor is a pulse monitor, also called a photoplethysmograph, which typically incorporates an incandescent lamp or light emitting diode (LED) to trans-illuminate an area of the subject, e.g. an appendage, which contains a sufficient amount of blood. FIG. 1 schematically illustrates the photoplethysmographic phenomenon. The light from the light source 10 disperses throughout the appendage, which is broken down in FIG. 1 into non-arterial blood components 12, non-pulsatile arterial blood 14 and pulsatile blood 16, and a light detector 18, such as a photodiode, is placed on the opposite side of the appendage to record the received light. Due to the absorption of light by the appendage's tissues and blood 12, 14 and 16, the intensity of light received by the photodiode 18 is less than the intensity of light transmitted by the LED 10. Of the light that is received, only a small portion (that effected by pulsatile arterial blood 16), usually only about two percent of the light received, behaves in a pulsatile fashion. The beating heart of the subject, and the breathing of the subject as discussed below, creates this pulsatile behavior. The "pulsatile portion light" is the signal of interest and is shown at 20, and effectively forms the photoplethysmograph. The absorption described above can be conceptualized as AC and DC components. The arterial vessels change in size with the beating of the heart and the breathing of the patient. The change in arterial vessel size causes the path length of light to change from $d_{min}$ to $d_{max}$. This change in path length produces the AC signal 20 on the photo-detector, $I_L$ to $I_H$. The AC Signal 20 is, therefore, also known as the photo-plethysmograph.

The absorption of certain wavelengths of light is also related to oxygen saturation levels of the hemoglobin in the blood transfusing the illuminated tissue. In a similar manner to the pulse monitoring, the variation in the light absorption caused by the change in oxygen saturation of the blood allows for the sensors to provide a direct measurement of arterial oxygen saturation, and when used in this context the devices are known as oximeters. The use of such sensors for both pulse monitoring and oxygenation monitoring is known and in such typical uses the devices are often referred to as pulse oximeters. These devices are well known for use in humans and large mammals and are described in U.S. Pat. Nos. 4,621,643; 4,700,708 and 4,830,014 which are incorporated herein by reference.

Current commercial pulse oximeters do not have the capability to measure breath rate or other breathing-related parameters other than blood oxygenation. An indirect (i.e. not positioned within the airway or airstream of the subject), non-invasive method for measuring breath rate is with impedance belts.

It is well established that it is critical to properly control anesthesia levels of a patient, or subject. In dealing with non-human subjects in animal research applications, having specialized anesthesiologists or specialized equipment is simply not an option for researchers. The use of breath-related parameters and heart-related parameters from easily applied non-invasive sensors to automate or assist in the control of proper anesthesia levels of a subject would be of great assistance. In a similar manner, simple, easy feedback for proper ventilation control from non-invasive, easily applied sensors in animal research applications would be very beneficial. Obviously, such advances would not be limited to animal research as non-invasive physiologic measurements can be very useful for human applications as well.

It is an object of the present invention to minimize the drawbacks of the existing systems and to provide medical devices and techniques for deriving cardiac and breathing parameters of a subject from extra-thoracic blood flow measurements and for controlling the ventilation levels and the anesthesia levels of a subject based upon said measurements.

SUMMARY OF THE INVENTION

It is noted that, as used in this specification and the appended claims, the singular forms "a," "an," and "the" include plural referents unless expressly and unequivocally limited to one referent. For the purposes of this specification, unless otherwise indicated, all numbers expressing any parameters used in the specification and claims are to be understood as being modified in all instances by the term "about." All numerical ranges herein include all numerical values and ranges of all numerical values within the recited numerical ranges.

The various embodiments and examples of the present invention as presented herein are understood to be illustrative of the present invention and not restrictive thereof and are non-limiting with respect to the scope of the invention.

At least some of the above stated objects are achieved with a method of utilizing a conventional pulse oximeter signal to derive breath rate. As understood by those of ordinary skill in the art a pulse oximeter is applied to the subject with a simple externally applied clip. Thus, in addition to getting oxygen saturation and heart rate from a pulse oximeter, the pulse oximeter according to the present invention can derive breath rate.

A measurement of breath rate from a pulse oximeter was first made commercially available in December 2005 by the assignee of the present application, Starr Life Sciences and is provided in the MouseOx™ device that was particularly designed for use with small mammals, namely rats and mice. In this device, the breath rate is obtained by screening out the frequency band around the heart rate point on the Fast Fourier Transform (known as FFT) that is used to identify the heart rate. The next largest amplitude to the left (or lower frequency) of the heart rate rejection band on the FFT was considered to be the breath rate. The value is then simply averaged then displayed on the screen to the user. Although useful there is room to greatly improve this calculation methodology to assure consistent accurate results.

The currently preferred breath rate algorithm works, in a general sense, by selectively filtering the heart rate from the light signal, then reconstructing the breath signal in the absence of the heart rate.

In addition to calculating a numerical breath rate using only pulse oximeter inputs, the present invention also provides a display of the breath rate signal, which is presented as the Breath Pleth (short for plethysmograph). The signal is derived from the inverse FFT of the calculations described above. It is preferred if the Breath Pleth signal is illustrated congruently with the heart signal. The reason for displaying the signals congruently is to avoid confusion over which signal represents breathing, and to illustrate the underlying breathing waveform in conjunction with the heart signal. The utility of this plot is to provide a visual sense of the relative breath rate as compared with heart rate, and to allow the user to see that the heart rate and breathing signals are superimposed on the raw infrared light signal. One can also deduce a relative magnitude between the signal strength due to the heart pulse, and that due to breathing.

In addition to the breath rate calculation from the pulse oximeter measurements, the present system provides additional breath and heart-related parameters other than the conventional heart rate and blood oxygenation. Namely the present system can calculate and display arterial distention measurements. The distention measurements are calculated using Beer's Law mathematics, in conjunction with the current calculation of oxygen saturation. There are two types of distention. The first, called pulse distention, is a measurement of the arterial distention which results from the blood pulse to the periphery due to cardiac pumping. The second, called breath distention, is a measurement of the arterial distention which results from the pulse of blood to the periphery due to breathing effort and its effect on thoracic arterial vasculature.

As will be described below, these measurements can be particularly useful to assist in control of anesthesia levels and ventilation controls. The user can employ the measured distention to assess the strength and quality of signals for making all sensor measurements. Further, the distention measurements, such as pulse distention, can be used to assess changes in peripheral blood flow either by changes in cardiac output or by changes in vaso-active response. The breath distention measurements may be used to assess intrapleural or intrathoracic pressure. The breath distention measurements may be used to assess work of breathing of the subject. The distention measurements may have many other clinical and research applications.

A measurement of pulse distention from a pulse oximeter was first made commercially available in December 2005 by the assignee of the present application, Starr Life Sciences and provided in the MouseOX™ device that was particularly designed for use with small mammals, namely rats and mice. Breath distention measurements from pulse oximetry systems have not been previously commercially available.

Preferably the measured pulse and breath distention measurements are displayed together on the same plot to the user. The utility of showing them together is that pulse distention can be used as a sort of baseline. The relative level of breath distention can then be used as an indicator of work of breathing. Since both are derived from changes in peripheral blood flow due to their respective mechanisms, if they both have the same magnitude, then both are affecting the peripheral blood flow by the same amount. In the general case, one would expect the blood pulse to provide a greater peripheral blood flow than would breathing effort. However, if breath distention is greater than pulse distention, the subject is likely laboring hard to breathe, a condition that often results form too much anesthesia.

The applicants have found that an increase in the breath distention measurement coupled with a decrease in the blood oxygenation and a drop in one or both of the breath rate and the heart rate is indicative of the subject moving to a higher or deeper anesthesia level. The technician can observe such trends and compensate accordingly. Additionally, appropriate thresholds can be incorporated into the system to provide alarms and/or automated anesthesia controls to automate the process. These parameters are also indicative of the subject moving to an undesired lower anesthesia level and the present system provides this information to the user as well. Alarms and/or automated anesthesia controls can be incorporated in response to detected significant movements in the anesthesia levels.

The applicants have found that "gasping" of the subject can be detected and is also typically indicative of a too high or deep of a level of anesthesia, and this can be used to control the anesthesia levels by giving appropriate feedback to the user. Further, applicants have found that, at least in mice, a breath distention measurement that is roughly equal to or less than the pulse distention is indicative of proper anesthesia levels and proper ventilation settings. An increase in the breath distention measurement relative to the pulse distention measurement can be used as an indicator for possible improper ventilation settings. Note that it is not necessary to compare pulse and breath distention measurements simultaneously to draw such conclusions, but viewing them together can show that the effect is only on one or the other distention measurement, and not both. The relative ratio between the breath distention and the pulse distention measurements and the blood oxygenation measurement can be used to indicate proper ventilator setting with thresholds being set to automate the system (i.e. measurements beyond the set thresholds will activate "alarms" and/or automate adjustments to the ventilator).

In one non-limiting aspect of the present invention a non-invasive pulse oximetry system comprises a light source emitting at least two light signals having distinct wavelengths directed at an appendage of a subject; and a light receiver mounted adjacent to said appendage and which receives said light signals; wherein the pulse oximetry system derives at least a heart rate value, a blood oxygenation value and a breath distention value from said received light signals. The system may derive a breath rate that is calculated by filtering the received signals to remove the heart rate component thereof, then reconstructing a breath signal in the absence of the heart rate components and wherein the breath rate is calculated using the breath signal. The breath components of the received signals may be filtered prior to reconstructing the breath signal. The system may calculate arterial pulse distention measurements.

In one non-limiting aspect of the present invention a non-invasive pulse oximetry system comprises a light source adapted to be attached to an external appendage of a subject and configured to emit at least two distinct wavelengths of light directed at the appendage; and a receiver adapted to be attached to the external appendage of a subject and configured to receive the light from the light source that has been directed at the appendage and generating received signals there from, wherein the pulse oximetry system derives a breath rate of the subject from the received signals, wherein the breath rate is calculated by filtering the received signals to remove heart rate components thereof, then reconstructing a breath signal in the absence of the heart rate components and wherein the breath rate is calculated using the reconstructed breath signal.

In one non-limiting embodiment a non-invasive pulse oximetry system for a small mammal comprises a light source adapted to be attached to an external appendage of a small mammal and configured to emit at least two distinct wavelengths of light directed at the appendage; and a receiver adapted to be attached to the external appendage of a subject small mammal and configured to receive the light from the light source that has been directed at the appendage and generating received signals there from, wherein the pulse oximetry system derives a breath rate of the subject from the received signals. The system may be mounted to the tail of a subject animal.

In one non-limiting embodiment of the present invention a non-invasive pulse oximetry system comprises a light source adapted to be attached to an external appendage of a subject and configured to emit at least two distinct wavelengths of light directed at the appendage; and a receiver adapted to be attached to the external appendage of a subject and configured to receive the light from the light source that has been directed at the appendage and generating received signals there from, wherein the pulse oximetry system derives at least one physiologic parameter of the subject from the received signals by performing an FFT on at least one time domain signal to generate a frequency domain representation of the at least one time domain signal, filtering the transformed time domain signal in the frequency domain, performing an inverse FFT on the filtered FFT signal to form a filtered time domain signal, and calculating the at least one physiologic parameter by measuring the filtered time domain signal.

These and other advantages of the present invention will be clarified in the brief description of the preferred embodiment taken together with the drawings in which like reference numerals represent like elements throughout.

BRIEF DESCRIPTION OF THE DRAWINGS

FIG. 5 is a graph of a representative signal of the raw-time domain signal from the pulse oximeter of FIGS. 2-4;

FIG. 6 is a graph of an FFT of the signal of FIG. 5;

FIG. 7 is a graph of the FFT of FIG. 6 with the heart components thereof filtered out in accordance with the present invention;

FIG. 8 is a graph of the FFT of FIG. 7 with the breath component filter applied in accordance with one aspect of the present invention;

FIG. 9 is a graph of a calculated breath signal from the FFT of FIG. 8;

DESCRIPTION OF THE PREFERRED EMBODIMENTS

Figure 1:
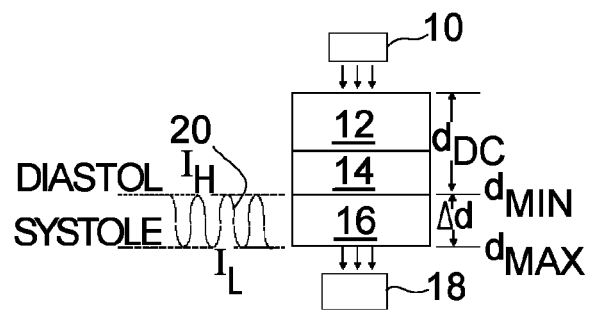
FIG. 1 schematically illustrates the photoplethysmographic phenomenon as generally known in the art.
Figure 2:
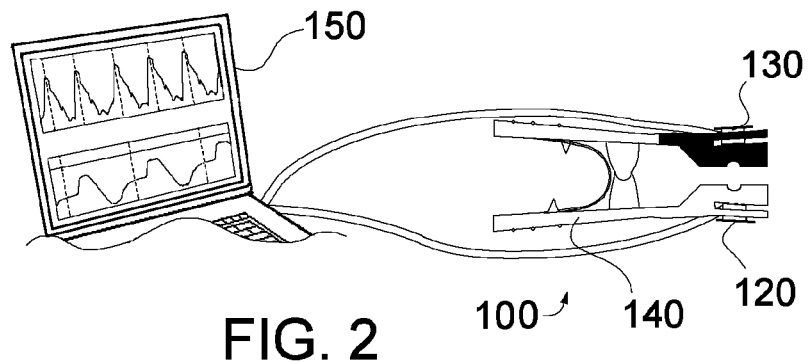
FIG. 2 is a schematic view of a pulse oximeter system according to one aspect of the present invention in which the pulse oximetry system is designed for small mammals such as mice and rats.
Figure 3:
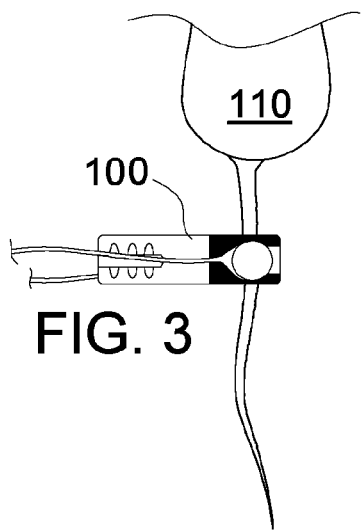
FIGS. 3-4 are perspective views of the pulse oximeter of FIG. 2 coupled to a subject, namely a mouse.
Figure 4:
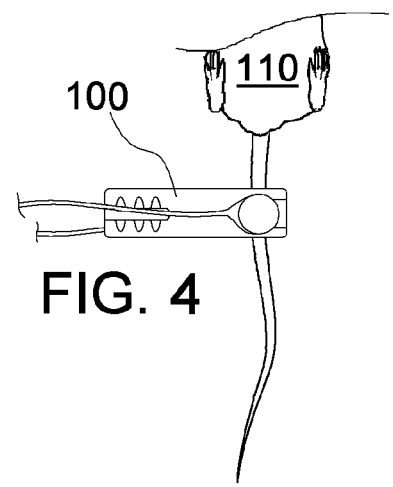

FIGS. 2-4 illustrate a pulse oximeter system 100 according to one aspect of the present invention in which the pulse oximetry system 100 is designed for subjects 110, namely small mammals such as mice and rats. The system 100 includes a conventional light source 120, conventionally a pair of LED light sources one being infrared and the other being red. The system 100 includes a conventional receiver 130, typically a photo-diode. The light source 120 and receiver 130 are adapted to be attached to an external appendage of a subject 110, and may be secured to a spring-biased clip 140 or other coupling device such as tape adhesives or the like. FIGS. 2-4 illustrate a specialized clip from Starr Life Sciences that is configured to securely attach to the tail of a subject 110, but any conventional clip could be used. The system 100 is also coupled to a controller and display unit 150, which can be a lap top computer. The use of a lap top computer as opposed to a dedicated controller and display system 150 has advantages in the research environment.

The system 100 will calculate the heart rate and blood oxygenation for the subject 110 as generally known in the art of photoplethysmograghy, and does not form the basis of the present invention. Where the subject 110 is a rodent, such as a mouse or rat, care must be taken to obtain accurate heart rate and oxygenation readings with conventional pulse oximeters due to the physiology of the subjects. Starr Life Sciences have developed pulse oximeters that accommodate rodents under the MouseOx™ brand name. For the purpose of this application the calculation of the pulse rate, pulse signal, and blood oxygenation will be considered as conventional.

A first measurement of breath rate from a pulse oximeter was first made commercially available in December 2005 by the assignee of the present application, Star Life Science and provided in the MouseOx™ device that was particularly designed for use with small mammals, namely rats and mice. In this first method, an FFT, represented in FIG. 6, is created for a received signal from the infrared LED in the time-domain, represented in FIG. 5. The breath rate is obtained by screening out the frequency band around the heart rate point on the FFT, represented in FIG. 6, that is used to identify the heart rate. The heart rate is effectively the largest peak shown in the FFT. The peak to the right of the FFT represents a first harmonic of the heart rate. The peak to the left of the heart rate on the FFT represents the measured breath rate.

The frequency band around the heart rate peak is preferably proportional (through a linear function or other relationship) to the heart rate itself, whereby the band will become larger for larger heart rates. This expanding filter band will accommodate the spreading of the illustrated peak that is expected at the higher measured heart rates. The filtering of the band is required to be sure that the peak measuring algorithm does not merely select the cut-off point of the heart rate peak as a calculated, but erroneous, breath rate. The next largest amplitude to the left (or lower frequency) of the heart rate rejection band on the FFT is considered to be the breath rate in this original methodology. The breath rate value is then simply averaged then displayed on the screen to the user. Although useful there is room to greatly improve this breath rate calculation methodology to assure consistent accurate results.

A preferred breath rate algorithm works, in a general sense, by selectively filtering the heart rate from the infrared light signal, then reconstructing the breath signal in the absence of the heart rate.

Specifically, the algorithm for obtaining a breath signal is as follows: Similar to the first method, an FFT, represented in FIG. 6, is created for a received signal from the infrared LED in the time-domain, represented in FIG. 5. In FIG. 6, the large spike is the heart rate, the small spike to the right is a harmonic of the heart rate, and the small spike to the left is the breathing signal. Consequently, the frequency located at the highest amplitude point in the FFT is considered to represent the heart rate. Because data used in the FFT occur over a span of time, the heart rate can naturally drift during this period, causing the frequency content at the peak amplitude point on the FFT to be spread over a few surrounding frequency bins.

The preferred breathing rate calculation method is to first remove all heart rate-derived frequency content from the FFT signal, called heart components of the signal. The algorithm chooses a lower threshold to the lower end of the peak heart rate frequency that defines the point above which all content will be removed. This can be done by digital filtering, but also by simply zeroing all frequency bins to the right of the lower threshold cutoff of the heart rate spike all the way to the end of the FFT. The lower threshold is chosen by an algorithm that is based on the mean value of the heart rate. The lower threshold is farther from the heart rate (i.e., the heart rate band of the FFT is larger) at high heart rates, and closer to the heart rate peak at low heart rates. It is desired to have the heart rate band to be as narrow as possible, in order to retain the largest possible breathing frequency spectrum. FIG. 7 illustrates a sample of the heart components removed from the FFT in the breathing rate calculation method of the present invention.

A peak detection algorithm is then used to identify the largest peak remaining in the FFT. The largest remaining peak is believed to be indicative of the breathing rate, however the preferred method performs a "breathing component filtering" on this remaining data.

This filtering application operates as follows: the initial breathing peak is compared with the rest of the remaining bandwidth. If the chosen breathing peak is "significantly stronger" than the others, then the breathing filtering is effectively a zeroing of all frequency bins a minimum number of bins to the right of this peak. The minimum number of bins has been found to be 0-3 and most preferably 2. This result is shown in FIG. 8. Significantly stronger means that the value of the "breathing peak" is greater than a predetermined factor of ALL of the other values with the heart components removed. 1.5 has been used effectively as the predetermined factor for calculating the relative strength of the breathing peak. If the chosen peak is only "moderately stronger" than the remaining peaks, then the next highest peak to the left of the strongest breathing peak is selected, and then all points on the FFT a minimum number to the right of this new peak are zeroed out resulting, effectively, in a graph as shown in FIG. 8 (except the Breathing filter has "pushed" the remaining breathing signal components to the lower frequencies). "Moderately stronger" means that less than a critical number, such as ½, of all the remaining points (but at least some of the remaining points) fail to satisfy the significantly stronger requirement discussed above. Finally, if the original chosen breathing peak is only "weakly stronger" than the remaining peaks, then the breathing component filter will identify the next two highest peaks to the left of the strongest peak, choose the one further to the left, then zero all points a minimum number of bins to the right of this new peak. Weakly stronger will mean that more than a critical number, such as ½, of all the remaining points fail to satisfy the significantly stronger requirement discussed above.

The next step in the process is to conduct an inverse FFT on the remaining frequency content as shown in FIG. 8. The breathing frequency is then contained in this time-domain signal, as represented in FIG. 9. A peak and valley detection algorithm, graphically shown in FIG. 9, is then used to find the breath rate. This breathing rate value is calculated from a number of separate, serial FFT-inverse FFT pairs, and is displayed on the screen to the user.

Figure 10:
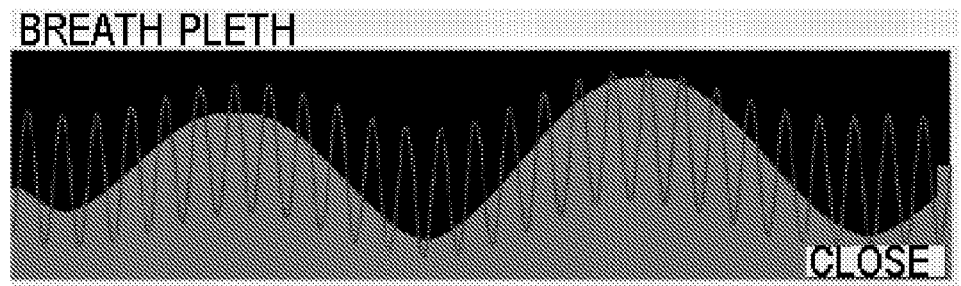
FIG. 10 is a representative sample of a combined display of the calculated breath signal and combined heart signal from the system according to the present invention.

In addition to calculating a numerical breath rate, the present invention also provides a display of the breath rate signal, which is called the Breath Pleth (short for plethysmograph). The signal is derived from the inverse FFT calculations described above. An example of the Breath Pleth screen is given in FIG. 10. In this picture, there are two plots. The underlying wave-shape represents the breathing waveform or signal. As it is depicted here, the actual plot of the breathing signal would be the envelope of that wave shape. The reason for displaying it in this manner is to avoid confusion over which signal represents breathing, and to illustrate the underlying breathing waveform in conjunction with the combined heart signal. This heart signal is presented in the other line waveform (at a significantly higher frequency). This signal contains not only the heart rate, but all frequency content in the received infrared light signal, and thus is referred to in this application as the combined heart signal and also the raw signal. The utility of this combined plot is to provide a visual sense of the relative breath rate as compared with heart rate, and to allow the user to see that the heart rate and breathing signals are superimposed on the raw infrared light signal. One can also deduce a relative magnitude between the signal strength due to the heart pulse, and that due to breathing.

In addition to the breath rate calculation from the pulse oximeter measurements, the present system 100 provides additional breath and heart-related parameters other than the conventional heart rate and blood oxygenation. Namely the present system can calculate and display arterial distention measurements. Distention measurements are calculated using Beer's Law mathematics, in conjunction with the current calculation of oxygen saturation. There are two types of distention. The first, called pulse distention, results from the blood pulse to the periphery due to cardiac pumping. The second, called breath distention, results from the pulse of blood to the periphery due to breathing effort and its effect on thoracic arterial vasculature.

To describe the physical meaning of a distention, one must first consider the column of light that passes between the LED and photodetector located on either side of the sensor clip. This light is absorbed by all intervening tissue, but we are interested only in arterial blood. Restricting received light information to arterial blood is done by looking for a change in light signal strength at either heart or breathing frequencies. This change literally corresponds to a change in local blood flow between the sensor heads that occurs as a result of either a cardiac output pulse, or a breath effort effect on the thoracic vasculature.

Next consider a cylindrical volume of arterial blood, where the cross-sectional area of the cylinder is defined by the lateral dimensions of the light column, while the height is defined by the quantity of arterial blood in the direction of the light path within that lateral area. Distention is then simply the change in height of the cylinder between the peak and valley of the attendant change mechanism (heart pulse or breath effort). In other words, if looking at pulse distention, which is derived from the cardiac pulse, the distention is due to the height of the blood flow change between systole and diastole. Likewise, the breath distention is the change in height derived from the endpoints of the breathing effort from inhale to exhale. Both distention measurements are given in linear dimensional units (e.g. μm). Current commercial pulse oximeters, other than the current MouseOx™ product of Starr Life Sciences, do not provide the user the capability to measure either of these distention values, and there is no known alternative method for making either of these measurements.

Pulse distention can be used by the operator to assess the strength and quality of signals for making all sensor measurements to evaluate the operation of the system. Further, It can be used to assess changes in peripheral blood flow either by changes in cardiac output or by changes in vaso-active response. Pulse distention is calculated from Beer's Law. It uses the light strength measured at systole and diastole in its calculation. The algorithm is as follows: (a) All signal filtering, both analog and digital is removed from the received raw infrared light signal; (b) The peaks and valleys of the received infrared light signal are detected; (c) For every peak and valley pair, the ratio of the peak and valley magnitude is used in the Beer's Law formulation to obtain pulse distention; and a few pulse distention values are averaged, then displayed both numerically and graphically.

Breath distention is a new parameter for researchers to utilize. The utility of breath distention includes that it can be used to assess intrapleural or intrathoracic pressure, and that it may be used to assess work of breathing. Further, it may be used to assess the level of anesthesia. Breath distention is also calculated from Beer's Law. The breath distention is calculated from the inverse FFT signal as described above. A simple algorithm of its derivation is given as follows: (a) From the description of the breath rate calculation algorithm given above, we start with the FFT signal from which the heart rate is removed only (FIG. 7), before additional frequency content clipping occurs with the breathing component filtering. Starting with this FFT, all original signal filtering, both analog and digital is removed by compensating the FFT amplitudes at each frequency bin, based on original filtering; (b) Once the filtering has been compensated, an inverse FFT is conducted; (c) The peaks and valleys of the inverse FFT time-domain breathing signal are identified; (d) All of the valid peaks are averaged, then all of the valid valleys are averaged; (e) From the average peak and valley pair for each FFT dataset, the Beer's Law calculation is used to find the breath distention; and (f) A few breath distention values are averaged, then displayed both numerically and graphically.

Figure 11:
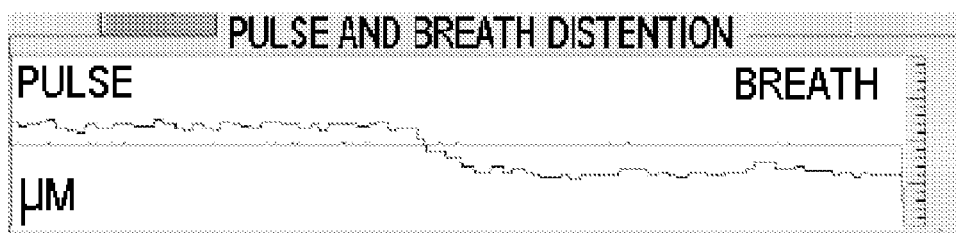
FIG. 11 is a representative example of a display of the pulse distention measurement and breath distention measurement in accordance with the system of the present invention.

Pulse and breath distention will be displayed together on the same plot in the Monitor Subject screen such as the display of the lap top 150, which is shown in FIG. 11. The utility of showing the distention measurements together is that pulse distention can be used as a sort of baseline. The relative level of breath distention can then be used as an indicator of work of breathing. Since both are derived from changes in peripheral blood flow due to their respective mechanisms, if they both have the same magnitude, then both are affecting the peripheral blood flow by the same amount. In the general case, one would expect the blood pulse to provide a greater peripheral blood flow than would breathing effort. However, if breath distention is greater than pulse distention, the animal is likely laboring hard to breathe, a condition that often results form too much anesthesia.

The present system 10 effectively provides a method of controlling the anesthesia level and/or ventilator settings of a subject that is receiving anesthesia and/or respiratory support through a ventilator. The method comprises the steps of providing the non-invasive sensor system 100 configured to calculate arterial pulse distention measurements of the subject, and using the measured arterial pulse distention measurements as indicators for at least one of proper and improper levels of anesthesia or proper and improper ventilator control settings. This method may be clarified in a review of FIGS. 12-17.

The applicants have found that an increase in the breath distention measurement coupled with a decrease in the blood oxygenation and a drop in one or both of the breath rate and the heart rate is indicative of the subject moving to a higher or deeper anesthesia level. The technician can observe such trends and compensate accordingly. Additionally, appropriate thresholds can be incorporated into the system to provide alarms and/or automated anesthesia controls to automate the process. These parameters are also indicative of the subject moving to an undesired lower anesthesia level and the present system provides this information to the user as well. Alarms and/or automated anesthesia controls can be incorporated in response to detected significant movements in the anesthesia levels.

Figure 12:
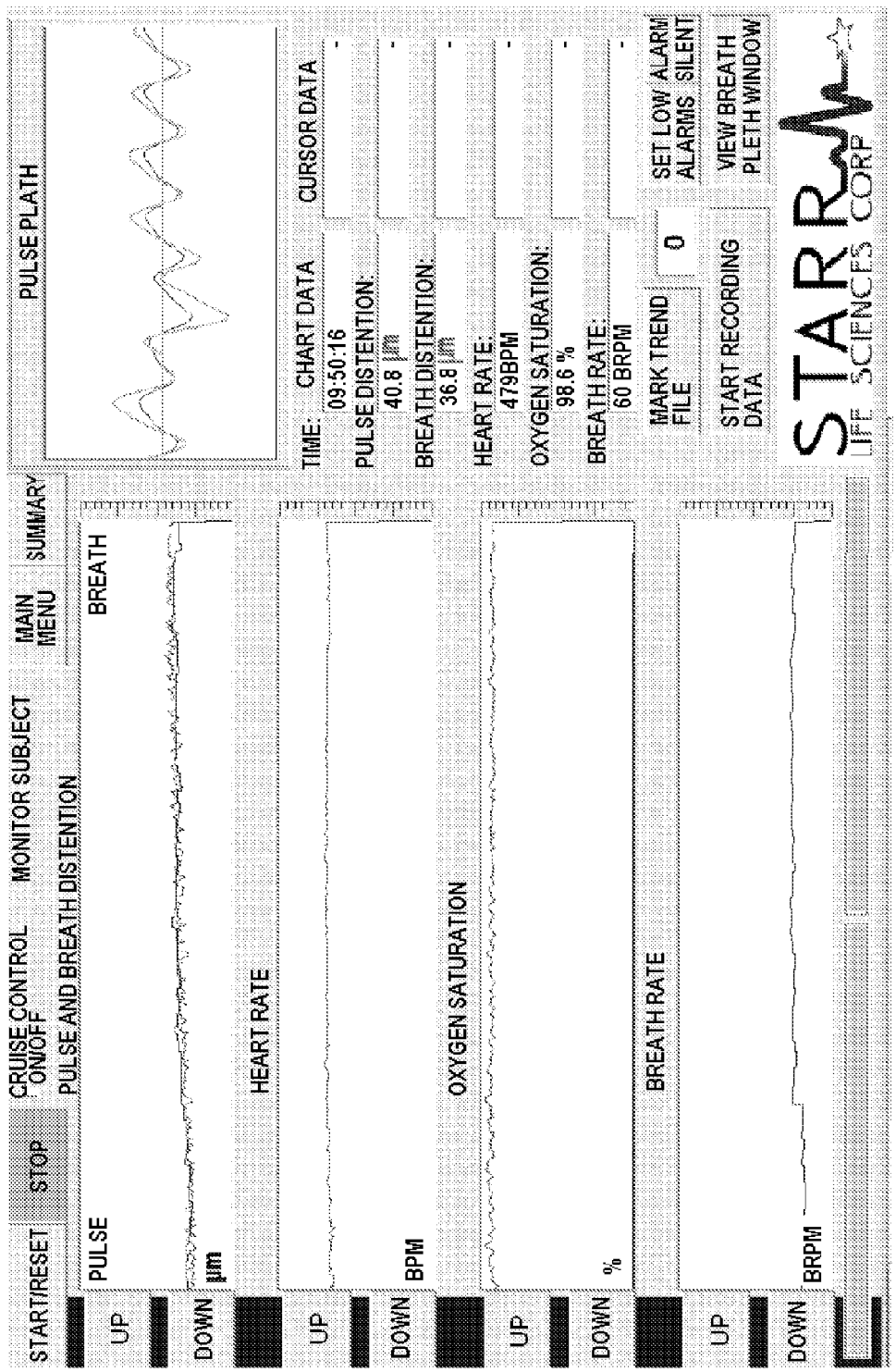
FIG. 12-14 are representative screen shots of the displayed parameters for properly anesthetized, under anesthetized and over anesthetized subjects, respectively.
Figure 13:
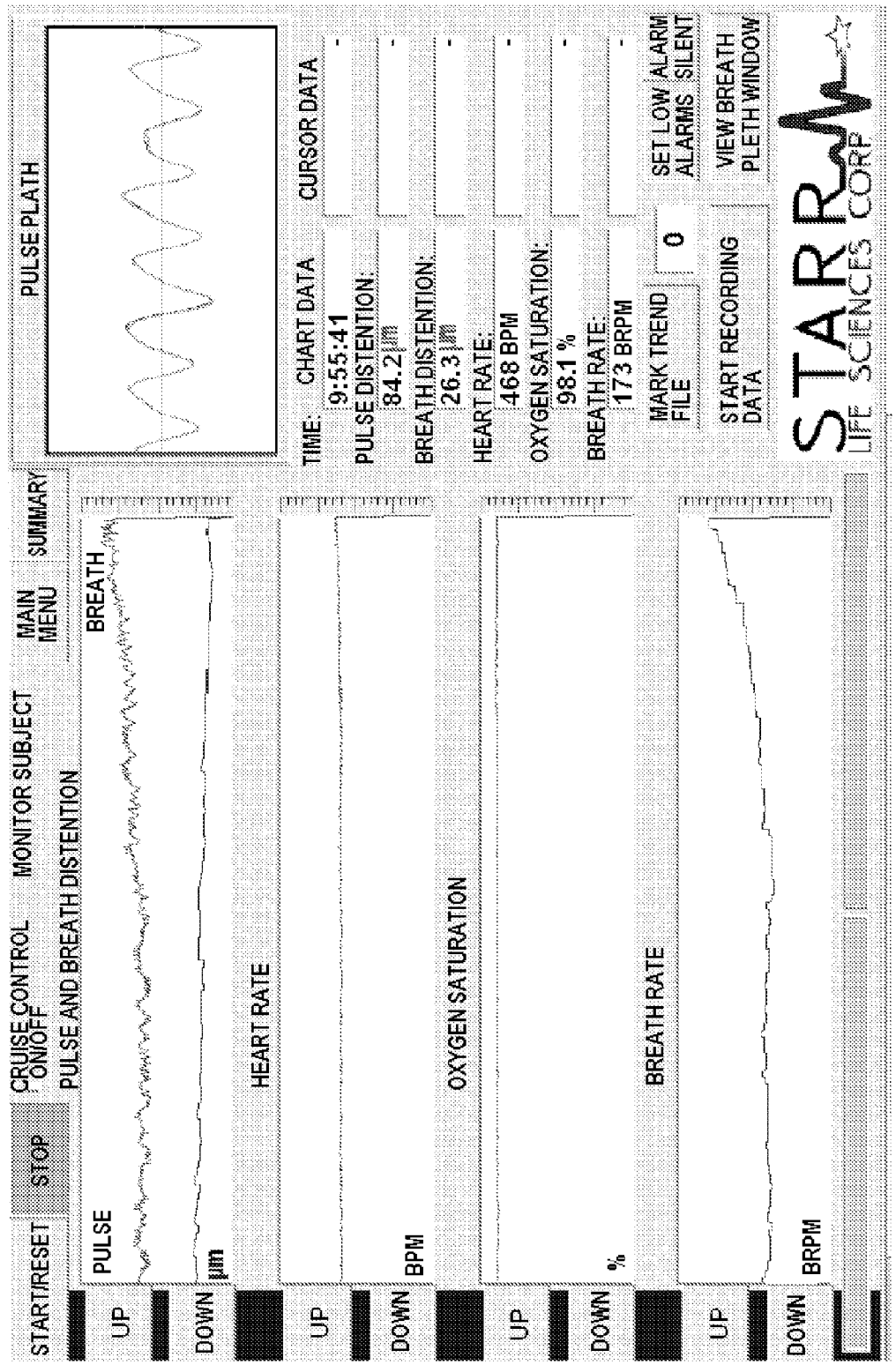
Figure 14:
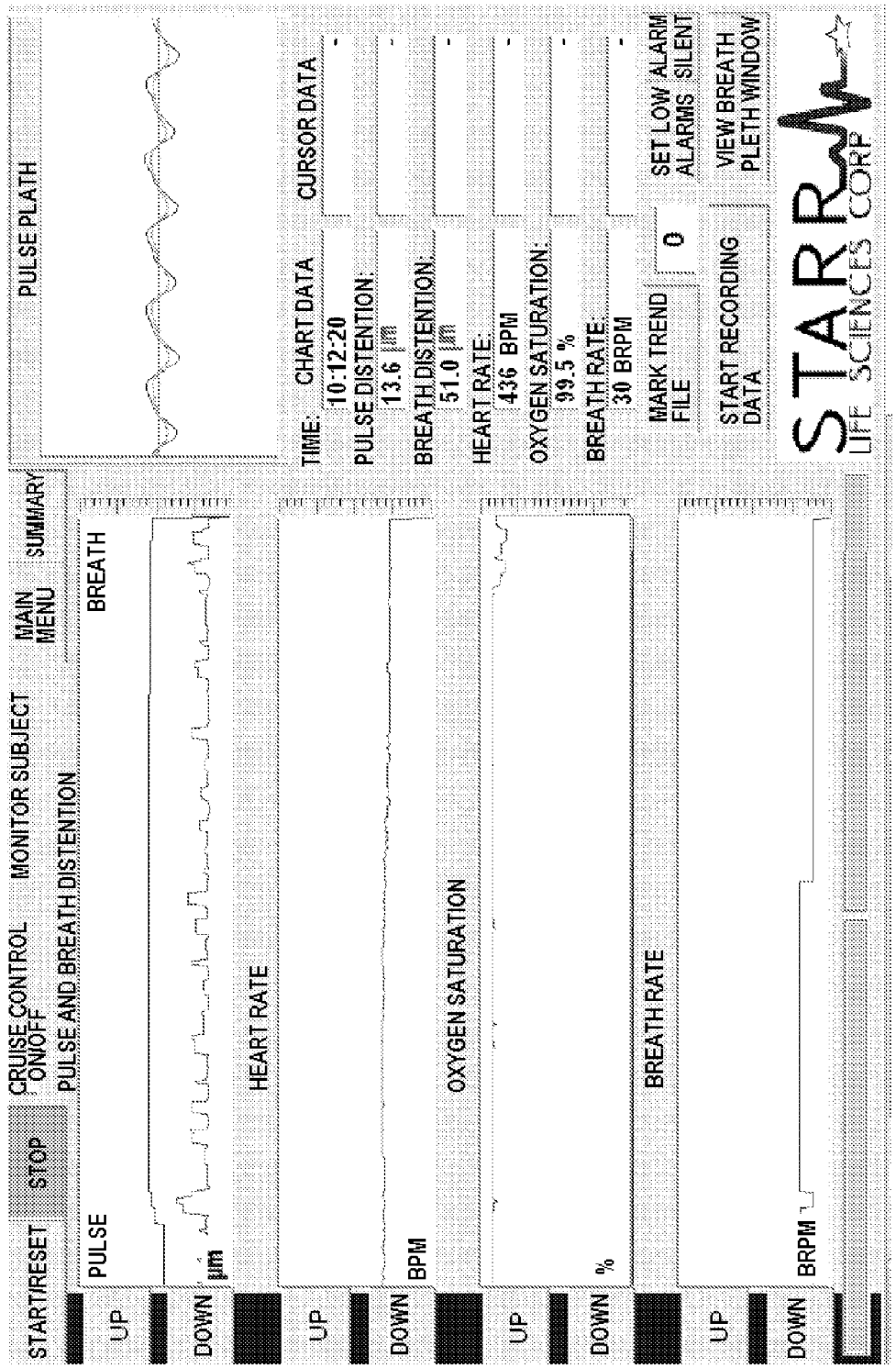

FIG. 12 is a screen clipping of the display of the system 100 for a subject, specifically a mouse, that is properly anesthetized. The pulse and breath distention are basically the same, the breath rate is stable and in the proper range. FIG. 13 is a screen clipping of a subject, again a mouse, that is too lightly anesthetized. This mouse is getting ready to wake up. The breath rate is increasing and the breath distention is much less than the pulse distention. FIG. 14 shows a screen clipping of a subject, again a mouse, that is too heavily anesthetized. This mouse is gasping and breathing at a very slow rate. This screen shot represents an extreme case and the breathing is very difficult to calculate because it is so slow. This results in that the breath distention is not updating often. However, when breath distention is able to update, as shown it is much higher than pulse distention providing important feedback to the operator.

Figure 15:
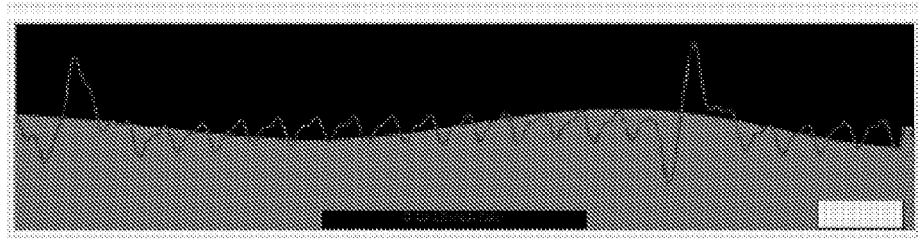
FIG. 15 is a representative sample of a combined display of the calculated breath signal and combined heart signal from the system according to the present invention illustrating a gasping subject.
Figure 16:
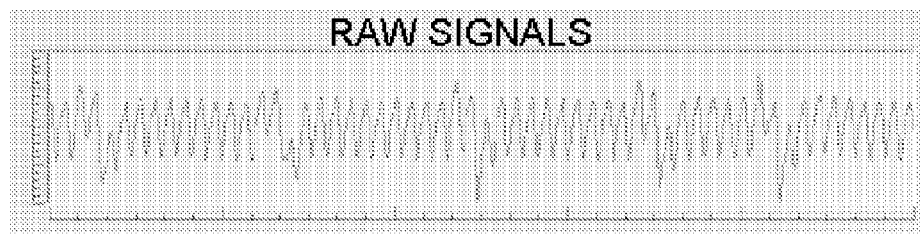
FIG. 16 is the raw-time domain signal from the pulse oximeter of FIGS. 2-4, associated with the gasping subject of FIG. 15.
Figure 17:
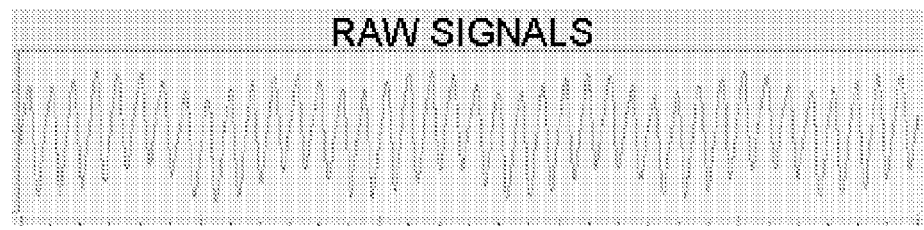
FIG. 17 is raw-time domain signal from the pulse oximeter of FIGS. 2-4, associated with normal response for comparison with the gasping subject of FIG. 16.

The applicants have found that "gasping" of the subject can be detected and is also typically indicative of a too high or deep of a level of anesthesia, and this can be used to control the anesthesia levels by giving appropriate feedback to the user. Further, the applicants have found that, at least in mice, a breath distention measurement that is roughly equal to or less than the pulse distention is indicative of proper anesthesia levels and proper ventilation settings. An increase in the breath distention measurement relative to the pulse distention measurement can be used as an indicator for possible improper ventilation settings. The relative ratio between the breath distention and the pulse distention measurements and the blood oxygenation measurement can be used to indicate proper ventilator setting with thresholds being set to automate the system (i.e. measurements beyond the set thresholds will activate "alarms" and/or automate adjustments to the ventilator). For example, consider FIGS. 15 and 16 which illustrate the graphical displays indicative of a deeply anesthetized subject, again a mouse. The screen clipping of the breath pleth window display of FIG. 15 shows a subject mouse that is too heavily anesthetized. This mouse is gasping and breathing at a very slow rate. The user can see in this window is that the mouse is gasping by the effect on the pulse signal. The pulse signal displayed here actually contains both of the distentions. The pulse distention is low for most of these heart beats then it will calculate high for this gasping beat. The breath distention will be high because it only looks at the effects cause by breathing. These parameters can be effectively used as guidance for both anesthesia levels and ventilation control.

The present system 100 is not intended to be restrictive of the invention. For example, all of these parameters can be measured using a partially-deflated blood pressure cuff, impedance belts or an arterial line. Further, the filtering is described above using inverse FFTs, but it can be done also with traditional digital and analog filtering methods. Additionally, reflective oximetry sensors, implanted sensors, clipless sensor, etc could be used. Only a light source (e.g., LED) and receiver (e.g., photodiode) are required.

Although the present invention has been described with particularity herein, the scope of the present invention is not limited to the specific embodiment disclosed. It will be apparent to those of ordinary skill in the art that various modifications may be made to the present invention without departing from the spirit and scope thereof. The scope of the present invention is defined in the appended claims and equivalents thereto.

What is claimed is:

1. A non-invasive pulse oximetry system comprising:
a controller;
a light source coupled to the controller and emitting at least two light signals having distinct wavelengths adapted to be directed at an appendage of a subject; and
a light receiver coupled to the controller and adapted to be mounted adjacent to said appendage and which receives said light signals;
wherein the controller of the pulse oximetry system derives at least a heart rate value, a blood oxygenation value, a breath rate and a breath distention value from said received light signals, wherein the breath distention value is associated with the height of the blood flow change in the appendage derived from the endpoints of the breathing effort from inhale to exhale, and wherein the system derives the breath rate that is calculated by filtering the received signals in the frequency domain to remove the heart rate component thereof, then reconstructing a time domain breath signal in the absence of the heart rate components and wherein the breath rate is calculated using the reconstructed breath signal.

2. The non-invasive pulse oximetry system of claim 1 wherein the breath components of the received signals are filtered prior to reconstructing the breath signal.

3. The non-invasive pulse oximetry system of claim 1 wherein the system calculates arterial pulse distention measurements, wherein the arterial pulse distention measurements are associated with the height of the blood flow change in the appendage derived from the endpoints of the cardiac effort between systole and diastole.

4. A non-invasive pulse oximetry system comprising:
A controller;
A light source coupled to the controller and adapted to be attached to an external appendage of a subject and configured to emit at least two distinct wavelengths of light directed at the appendage; and
A receiver coupled to the controller and adapted to be attached to the external appendage of a subject and configured to receive the light from the light source that has been directed at the appendage and generating received signals there from, wherein the controller of the pulse oximetry system derives a breath rate of the subject from the received signals, wherein the breath rate is calculated by transforming the received signals to the frequency domain, filtering the received signals to remove heart rate components thereof in the frequency domain, then reconstructing a breath signal in the time domain in the absence of the heart rate components and wherein the breath rate is calculated using the reconstructed breath signal in the time domain.

5. The non-invasive pulse oximetry system of claim 4 wherein the filtering the received signals to remove heart rate components thereof results in a filtered signal having breath components therein and wherein the breath components of the received signals are filtered prior to reconstructing the breath signal.

6. The non-invasive pulse oximetry system of claim 5 wherein the system calculates arterial pulse distention measurements, wherein the arterial pulse distention measurements are associated with the height of the blood flow change in the appendage derived from the endpoints of the cardiac effort between systole and diastole.

7. The non-invasive pulse oximetry system of claim 4 wherein the system calculates arterial pulse distention measurements, wherein the arterial pulse distention measurements are associated with the height of the blood flow change in the appendage derived from the endpoints of the cardiac effort between systole and diastole.

8. A non-invasive pulse oximetry system for a small mammal comprising:
A controller;
A light source coupled to the controller and adapted to be attached to an external appendage of a small mammal and configured to emit at least two distinct wavelengths of light directed at the appendage; and
A receiver coupled to the controller and adapted to be attached to the external appendage of a subject small mammal and configured to receive the light from the light source that has been directed at the appendage and generating received signals there from, wherein the controller of the pulse oximetry system derives a breath rate of the subject from the received signals and wherein the system calculates arterial pulse distention measurements, wherein the arterial pulse distention measurements are associated with the height of the blood flow change in the appendage derived from the endpoints of the cardiac effort between systole and diastole, and wherein the arterial pulse distention measurements is derived from a plurality of ratios of peak and valley ratios of the received signals.

9. The non-invasive pulse oximetry system of claim 8 wherein the system is mounted to the tail of a subject animal.

10. The non-invasive pulse oximetry system of claim 9 wherein the received signals includes heart rate components thereof and wherein the breath rate is calculated by filtering the received signals to remove the heart rate components thereof, then reconstructing a breath signal in the absence of the heart rate components and wherein the breath rate is calculated using the breath signal.

11. The non-invasive pulse oximetry system of claim 10 wherein the breath components of the received signals are filtered prior to reconstructing the breath signal.

12. A non-invasive pulse oximetry system comprising:
A controller;
A light source coupled to the controller and adapted to be attached to an external appendage of a subject and configured to emit at least two distinct wavelengths of light directed at the appendage; and
A receiver coupled to the controller and adapted to be attached to the external appendage of a subject and configured to receive the light from the light source that has been directed at the appendage and generating received signals there from, wherein the controller of the pulse oximetry system derives at least one physiologic parameter of the subject from the received signals by performing an FFT on at least one time domain signal to generate a frequency domain representation of the at least one time domain signal, filtering the transformed time domain signal in the frequency domain, performing an inverse FFT on the filtered FFT signal to form a filtered time domain signal, and calculating the at least one physiologic parameter by measuring the filtered time domain signal, wherein the system calculates arterial breath distention measurements of the subject wherein the breath distention measurements are associated with the height of the blood flow change in the appendage derived from the endpoints of the breathing effort from inhale to exhale.

13. The non-invasive pulse oximetry system of claim 12 wherein the system further derives a breath rate of the subject by reconstructing a time domain breath signal in the absence of heart rate components and wherein the breath rate is calculated using the reconstructed breath signal.

14. The non-invasive pulse oximetry system of claim 13 wherein the system further derives a heart rate of the subject by reconstructing a time domain heart signal in the absence of breath components and wherein the heart rate is calculated using the reconstructed heart signal.

15. The non-invasive pulse oximetry system of claim 13 wherein the system calculates arterial pulse distention measurements, wherein the arterial pulse distention measurements are associated with the height of the blood flow change in the appendage derived from the endpoints of the cardiac effort between systole and diastole.

16. The non-invasive pulse oximetry system of claim 12 wherein the system calculates arterial pulse distention measurements, wherein the arterial pulse distention measurements are associated with the height of the blood flow change in the appendage derived from the endpoints of the cardiac effort between systole and diastole.

* * * * *